United States Patent [19]

November

[11] 4,163,388
[45] Aug. 7, 1979

[54] CALORIMETER

[75] Inventor: Milton H. November, Hacienda Heights, Calif.

[73] Assignee: International Telephone and Telegraph Corporation, New York, N.Y.

[21] Appl. No.: 953,087

[22] Filed: Oct. 20, 1978

[51] Int. Cl.$^2$ .............................................. G01K 17/00
[52] U.S. Cl. ................................................. 73/190 CV
[58] Field of Search .................................... 73/190 CV

[56] References Cited

U.S. PATENT DOCUMENTS

| | | | |
|---|---|---|---|
| 2,026,179 | 12/1935 | Keith | 73/190 |
| 3,472,071 | 10/1969 | Toyoda et al. | 73/190 |
| 3,724,261 | 4/1973 | Kydd et al. | 73/190 |

Primary Examiner—Herbert Goldstein
Attorney, Agent, or Firm—A. Donald Stolzy

[57] ABSTRACT

The heat of combustion $K_1$ of a gas is determined by burning the gas in air in a chamber and cooling the combustion products with air to a final temperature equal to the air and gas input temperature. With mass flowmeters, the gas flowrate $W_1$, the cooling air flow rate $W_3$, a $T_2$ temperature sensor, and a sensor for the cooling air input temperature $T_3$ are employed with a computer to derive $K_1$ as follows:

$$K_1 = \frac{K_3 W_3 (T_1 - T_3)}{W_1}$$

where $K_3$ is the specific heat of the cooling air. Alternatively an outlet temperature $T_1$ may be substituted for $T_2$.

6 Claims, 2 Drawing Figures

CALORIMETER

BACKGROUND OF THE INVENTION

This invention relates to a system for producing an output proportional to the heat of combustion of a gas, and more particularly to a calorimeter or the like.

PRIOR ART STATEMENT

Austin, U.S. Pat. No. 3,853,474, issued Dec. 10, 1974, and Eads, U.S. Pat. No. 3,650,696, issued Mar. 21, 1972, disclose systems for enclosed gas combustion product analysis, but do not disclose any temperature control or analysis of the exothermal character of the reaction.

SUMMARY OF THE INVENTION

In accordance with the calorimeter of the present invention, the above-described and other disadvantages of the prior art are overcome by providing an implicit flow type feedback calorimeter.

BRIEF DESCRIPTION OF THE DRAWING

In the drawing, which illustrates an exemplary embodiment of the present invention.

DESCRIPTION OF THE PREFERRED EMBODIMENT

Figure 1:
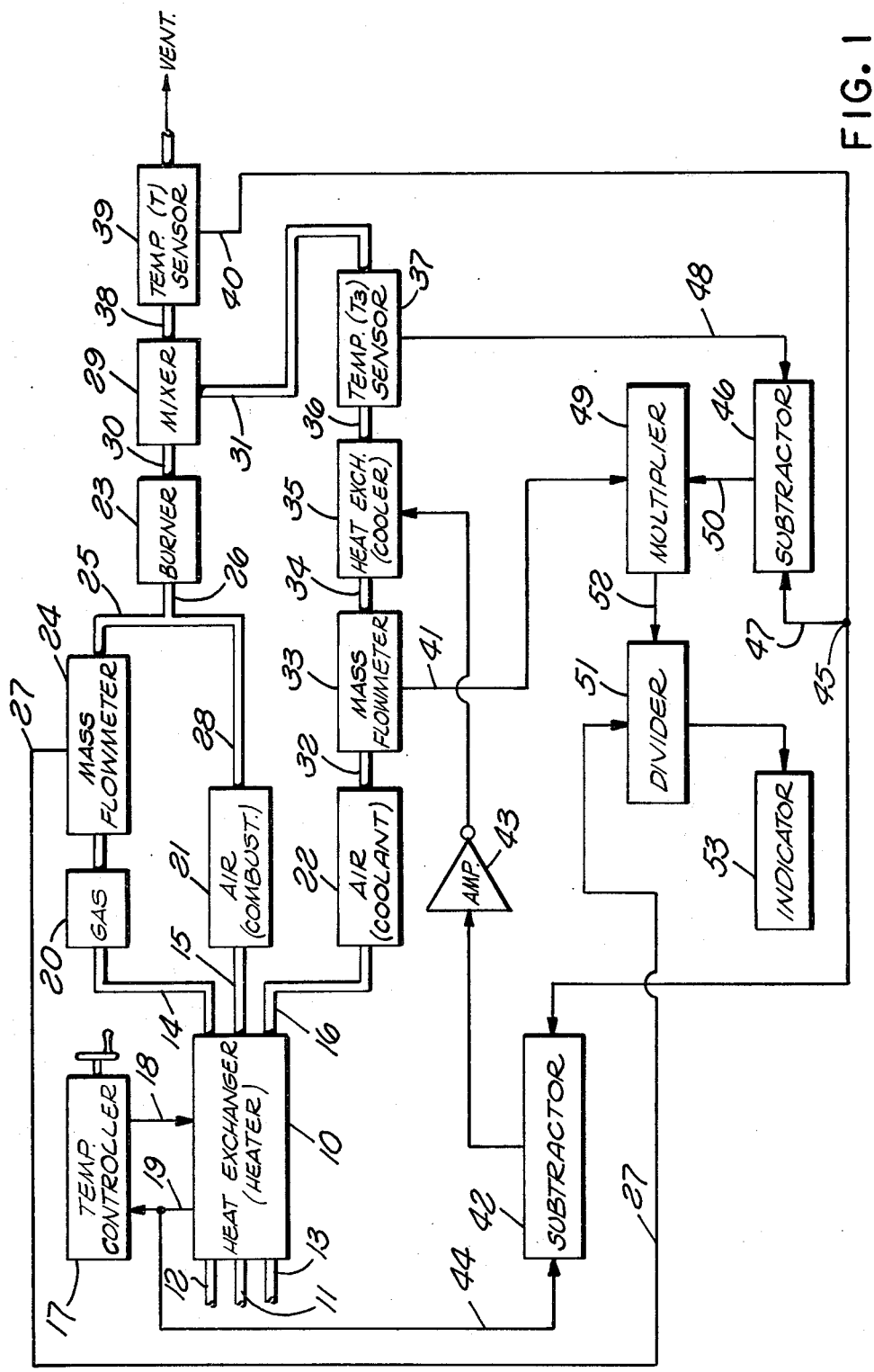
FIG. 1 is a block diagram of one embodiment of a calorimeter. constructed in accordance with the present invention.

In the FIGURE, combustible gas (e.g., methane or a hydrocarbon mixture) having a heat of combustion $K_1$ is supplied through a conventional heat exchanger 10 via a tube 12. Air flows in tubes 11 and 13 through heat exchanger 10. The gas in tube 14 and air in tubes 15 and 16 thus exit the heat exchanger 10 at the same inlet temperature $T_2$. Tubes 14, 15 and 16 are connected from or are the same tubes as tubes 12, 11 and 13.

A conventional temperature controller 17 may be used, if desired, to heat exchanger 10 to an inlet temperature $T_2$ that is preferably but not necessarily constant. The heat control may be applied over a lead 18. An electrical signal proportional to the temperature of heat exchanger may be measured with a Wheatstone bridge and thermistor or other conventional analog or digital source which may have an output lead 19.

An optional gas chamber 20, an optional air chamber 21, and an optional air chamber 22 are connected from tubes 14, 15 and 16, respectively. Chambers 20, 21 and 22 may be omitted if desired.

Chamber 20 is connected to a conventional enclosed burner 23 through a conventional mass flowmeter 24 and tubes 25 and 26. Flowmeter 24 has an electrical output lead 27 which carries an electrical analog or digital signal proportional to the mass flow rate $W_1$ of the gas.

Air from chamber 21 is introduced to burner 23 via tubes 28 and 26.

The combustion products in burner 23 are delivered to a conventional mixer 29 by a tube 30.

Air of a variable temperature $T_3$ is then mixed with the combustion products by introducing such air to mixer 29 through a tube 31.

Chamber 22 is connected to tube 31 by a series of components, namely, a tube 32, a mass flowmeter 33, a tube 34, a heat exchanger (cooler) 35, a tube 36, and a $T_3$ temperature sensor 37, all of which are conventional.

The temperature $T_1$ of the air and combustion products at the output of mixer 29 in tube 38 is detected by a conventional temperature sensor 39. Sensor 39 has an output lead 40 on which an electrical signal is sent proportional to the temperature $T_1$ sensed by 39.

Flowmeter 33 produces an electrical signal on an output lead 41 thereof proportional to the mass flow rate $W_3$ of air through flowmeter 33.

A conventional subtractor 42 and conventional amplifier 43 cause the air in tube 31 to be cooled to such an extent that the common temperature $T_1$ of the gas and air in tubes 14, 15 and 16 is the same as that indicated by the signal on lead 40. Note that subtractor 42 has inputs proportional to the temperatures in heat exchanger 10 via leads 19 and 44, and lead 40 through a junction 45.

Another conventional subtractor 46 has one input lead 47 from junction 45 and another input lead 48 from sensor 37.

A multiplier is provided at 49 which has input leads 41 and 50 from flowmeter 33 and subtractor 46, respectively.

A conventional divider 51 is provided with input leads 27 and 52 from flowmeter 24 and multiplier 49, respectively.

The output of divider 51 is connected to an indicator 53 which may be a voltmeter calibrated in British Thermal Units (BTU's) per pound, if desired.

OPERATION

Normally, the flow of air in tube 15 will supply oxygen at a rate somewhat greater than the stoichiometric rate.

There are two electrical circuits which perform different functions. Subtractor 42 and amplifier 43 complete a feedback loop to keep the mixture in tube 38 at the same temperature as the gas and air in tubes 14, 15 and 16. This is done by, through heat exchanger 35, reducing the temperature of the air in tube 31 in accordance with the output of amplifier 43.

The remaining circuit computes the heat of combustion of the gas. This computation is made as follows.

The product of the heat of combustion $K_1$ and the gas flow rate $W_1$ us equal to the heat per unit time absorbed by the air in tube 31, because the inlet and outlet temperatures $T_2$ and $T_1$, respectively, are maintained equal. The product of the temperature difference $(T_2-T_3)$ and the specific heat $(K_3)$-air flow rate $W_3$ product (in tube 31) is thus equal to $K_1 W_1$ or vice versa.

Thus:

$$K_1 W_1 = K_3 W_3 (T_2 - T_3) \tag{1}$$

$$K_1 = \frac{K_3 W_3 (T_2 - T_3)}{W_1} \tag{2}$$

The computer circuit thus computes $K_1$ by equation (2).

Due to the fact that the feedback circuit maintains the inlet and outlet temperatures the same, lead 47 may be disconnected from junction 45 and reconnected to lead 44, if desired.

The word "air" is hereby defined for use herein and in the claims to mean any source of oxygen by itself or in a suitable mixture for calorimetry or the like.

Alternatively:

$$K_1 = \frac{K_3 W_3 (T_1 - T_3)}{W_1}$$

Figure 2:
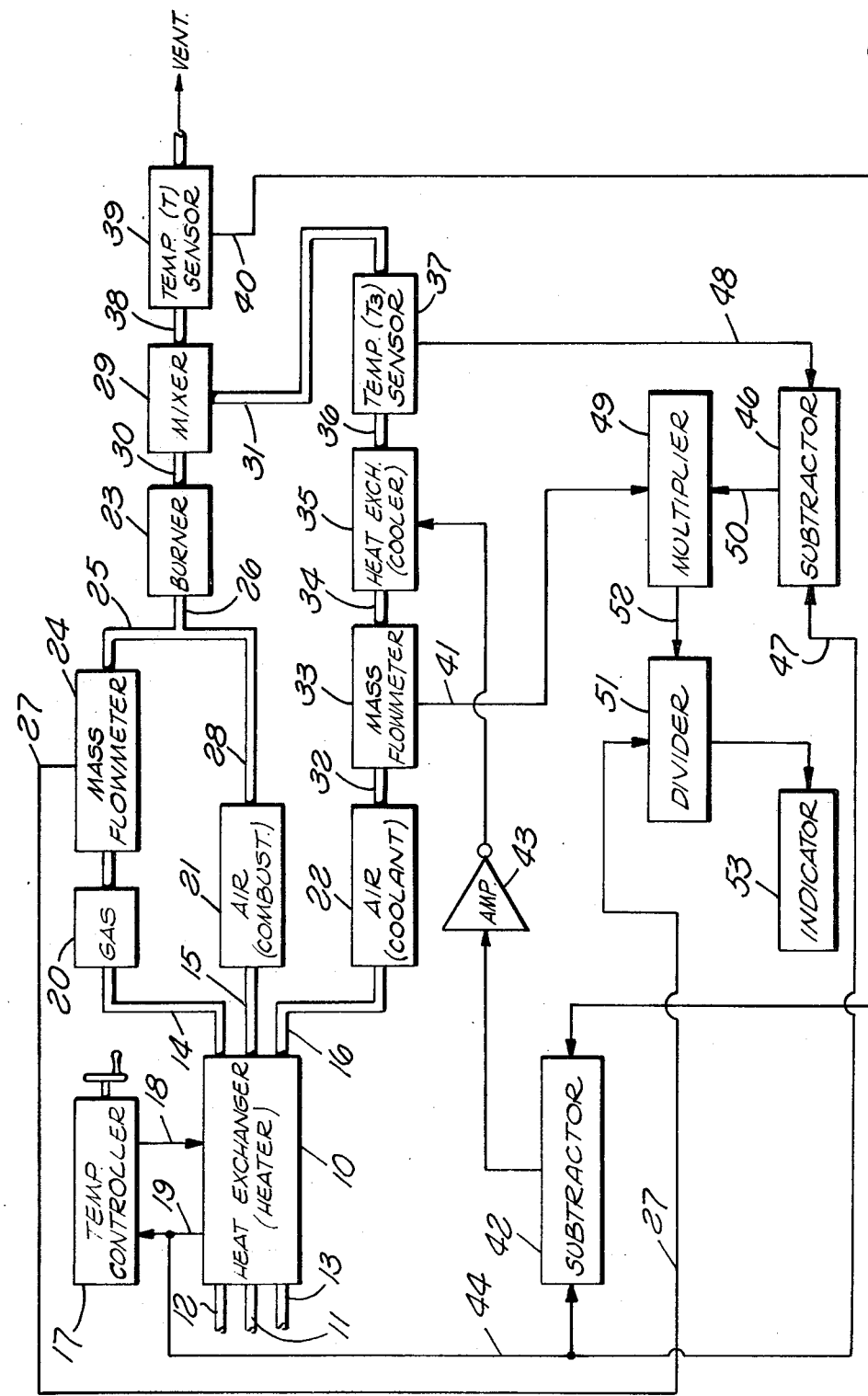
FIG. 2 is a block diagram of an alternative embodiment of the invention.

See FIG. 2.

What is claimed is:

1. A calorimeter comprising: first conduit means to carry a combustible gas, said first conduit means including a gas mass flowmeter; burner means including a combustion chamber having an inlet side; second conduit means to carry air at a flow rate approximately equal to that required to oxidize substantially all the combustible components of said gas, said first conduit means being connected to said combustion chamber on the inlet side thereof, said second conduit means also being connected to said combustion chamber inlet side; a first heater exchanger; a mixer connected from said combustion chamber; third conduit means to carry air, said third conduit means including an air mass flowmeter said first heat exchanger being actuable in a manner to maintain gas in said first conduit means and air in said second and third conduit means at the same inlet temperature $T_2$; second heat exchanger having an inlet and an outlet, said third conduit means being connected to the inlet of said second heat exchanger; a first sensor connected from said second heat exchanger outlet to said mixer to produce an output signal proportional to the temperature $T_3$ of the air entering said mixer; a second sensor for the final temperature at the output of said mixer; computer means responsive to the difference between said final temperature and said inlet temperature to drive said second heat exchanger to cool the air therein in a manner to maintain said final temperature equal to $T_2$; and means responsive to the output $W_1$ of said gas flowmeter, the output $W_3$ said air flowmeter, and said temperature $T_3$ and one of the other two temperatures for computing an output signal proportional to the term $$\frac{K_3 W_3 (T - T_3)}{W_1}$$

where $W_1$ is the mass flow rate of the gas, $W_3$ is the mass flow rate of the air in said third conduit means, and $K_3$ is the specific heat of the air flowing in said third conduit means, and T is one of the temperatures $T_1$ and $T_2$.

2. the invention as defined in claim 1, wherein utilization means is connected to receive the output of said computer means.

3. The invention as defined in claim 2, wherein said utilization means includes means to indicate the heat of combustion of said gas and is calibrated in thermal units per unit mass.

4. A calorimeter comprising: first conduit means to carry a combustible gas, said first conduit means including a gas mass flowmeter; burner means including a combustion chamber having an inlet side; second conduit means to carry air at a flow rate approximately equal to that required to oxidize substantially all the combustible components of said gas, said first conduit means being connected to said combustion chamber on the inlet side thereof, said second conduit means also being connected to said combustion chamber inlet side; a first heat exchanger; a mixer connected from said combustion chamber; third conduit means to carry air, said third conduit means including an air mass flowmeter, said first heat exchanger being actuable to maintain gas in said first conduit means and air in said second and third conduit means at the same inlet temperature $T_2$; second heat exchanger having an inlet and an outlet, said third conduit means being connected to the inlet of said second heat exchanger; a first sensor connected from said second heat exchanger outlet to said mixer to produce an output signal proportional to the temperature $T_3$ of the air entering said mixer; a second sensor for the final temperature at the output of said mixer; computer means responsive to the difference between said final temperature and said inlet temperature to drive said second heat exchanger to cool the air therein in a manner to maintain said final temperature equal to $T_2$; and means responsive to the output $W_1$ of said gas flowmeter, the output $W_3$ said air flowmeter, and said temperatures $T_2$ and $T_3$ for computing an output signal proportional to the term $$\frac{K_3 W_3 (T_2 - T_3)}{W_1}$$

where $W_1$ is the mass flow rate of the gas, $W_3$ is the mass flow rate of the air in said third conduit means, and $K_3$ is the specific heat of the air flowing in said third conduit means.

5. The invention as defined in claim 4, wherein utilization means is connected to receive the output of said computer means.

6. The invention as defined in claim 5, where said utilization means includes means to indicate the heat of combustion of said gas and is calibrated in thermal units per unit mass.

* * * * *